United States Patent [19]

Defossa et al.

[11] Patent Number: 5,589,594
[45] Date of Patent: Dec. 31, 1996

[54] PROCESS FOR THE PREPARATION OF CEPHEM PRODRUG ESTERS

[75] Inventors: Elisabeth Defossa, Idstein; Gerd Fischer, Limburg; Uwe Gerlach, Frankfurt am Main; Rolf Hörlein, Frankfurt am Main; Norbert Krass, Frankfurt am Main; Rudolf Lattrell, Königstein/Taunus; Ulrich Stache, Hofheim am Taunus; Theodor Wollmann, Hofheim am Taunus, all of Germany

[73] Assignee: Hoechst Aktiengesellschaft, Frankfurt am Main, Germany

[21] Appl. No.: 176,501

[22] Filed: Dec. 30, 1993

Related U.S. Application Data

[63] Continuation of Ser. No. 16,562, Feb. 11, 1993, abandoned.

[30] Foreign Application Priority Data

Feb. 14, 1992 [DE] Germany ............... 42 04 349.2

[51] Int. Cl.⁶ ................................................. C07D 501/02
[52] U.S. Cl. ............................................................. 540/228
[58] Field of Search ................................. 540/222, 228; 548/194

[56] References Cited

U.S. PATENT DOCUMENTS

| | | |
|---|---|---|
| 4,098,888 | 7/1978 | Ochiai et al. . |
| 4,152,329 | 5/1979 | Cahoy ................... 548/194 |
| 4,203,899 | 5/1980 | Ochiai et al. . |
| 4,205,180 | 5/1980 | Ochiai et al. . |
| 4,264,595 | 4/1981 | Numata et al. . |
| 4,278,793 | 7/1981 | Dürckheimer et al. . |
| 4,283,396 | 8/1981 | Heymes et al. . |
| 4,298,606 | 11/1981 | Ochiai et al. . |
| 4,355,160 | 10/1982 | Ochiai et al. . |
| 4,409,215 | 10/1983 | Takaya et al. . |
| 4,462,999 | 7/1984 | Takaya et al. . |
| 4,483,855 | 11/1984 | Nakao et al. . |
| 4,486,425 | 12/1992 | Nakao et al. . |
| 4,514,565 | 4/1985 | Ochiai et al. . |
| 4,668,783 | 5/1987 | Ochiai et al. . |
| 4,904,652 | 2/1990 | Takaya et al. . |
| 4,912,212 | 3/1990 | Ochiai et al. . |
| 4,935,508 | 6/1990 | Kamachi et al. ........... 540/222 |
| 4,948,898 | 8/1990 | Furlenmeir et al. ........ 546/311 |
| 4,973,684 | 11/1990 | Ochiai et al. . |
| 4,992,431 | 3/1991 | Heymes et al. . |
| 5,026,695 | 6/1991 | Takaya et al. . |
| 5,063,224 | 11/1991 | Mosher et al. . |
| 5,100,887 | 3/1992 | Adam et al. . |
| 5,114,959 | 5/1992 | Klausener ..................... 514/369 |
| 5,359,057 | 10/1994 | Furlenmeir et al. ........ 540/222 |

FOREIGN PATENT DOCUMENTS

| | | |
|---|---|---|
| 0034536B1 | 2/1981 | European Pat. Off. . |
| 0034536A2 | 2/1981 | European Pat. Off. . |
| 0029557A2 | 6/1981 | European Pat. Off. . |
| 0034536A3 | 8/1981 | European Pat. Off. . |
| 0049119A2 | 4/1982 | European Pat. Off. . |
| 0049118A2 | 4/1982 | European Pat. Off. . |
| 0134420A1 | 3/1985 | European Pat. Off. . |
| 0156771 | 10/1985 | European Pat. Off. . |
| 0156771A2 | 10/1985 | European Pat. Off. . |
| 0329008A2 | 8/1989 | European Pat. Off. . |
| 0334281A2 | 9/1989 | European Pat. Off. . |
| 0355821A2 | 2/1990 | European Pat. Off. . |
| 0379132A2 | 7/1990 | European Pat. Off. . |
| 0402806A1 | 12/1990 | European Pat. Off. . |
| 0514791A2 | 11/1992 | European Pat. Off. . |
| 0531875A2 | 3/1993 | European Pat. Off. . |
| 2556736A1 | 6/1976 | Germany . |
| 2560398C2 | 9/1983 | Germany . |
| 3804841A1 | 8/1989 | Germany . |
| 3809561 | 10/1989 | Germany . |
| 3919259A1 | 12/1990 | Germany . |
| 60-004189A | 1/1985 | Japan . |
| 60-004190A | 1/1985 | Japan . |
| 2110688 | 6/1983 | United Kingdom . |
| WO92/07840 | 5/1992 | WIPO . |

OTHER PUBLICATIONS

Arzneimittel Wirkungen, E. Mutschler (1981).
Angewandte Chemie, 24(3):186–197 (1985).
S. Torii et al., J. Org. Chem. 56:3633 (1991).
H. Kamachi et al., J. Antibiotics 41(11):1602 (1988).
K. Fujimoto et al., J. Antibiotics 40(3):370 (1987).
T. Nishimura et al., J. Antibiotics 40(1):81 (1987).
E. Defossa et al., Abstract No. 187, Cefdaloxime Pentexil Tosilate (HR916K): a Diastereomerically Pure Novel Oral Cephalosporinester: Synthesis and Antibacterial Activity In Vivo (Oct. 11–14, 1991).
D. Isert et al., Abstract No. 188, Cefdaloxime Pentexil Tosilate (HR916K): a Diastereomerically Pure Novel Oral Cephalosporinester with Outstanding Absorption Characteristics (Oct. 11–14, 1991).
"Cefpodoxime Proxetil", Drugs of the Future, 14(1):73–74 (1989).
"SCE-2174", Drugs of the Future, 13(3):231–233 (1988).
"Cerfuroxime Axetil", Drugs of the Future, 10(2):112–113 (1985).

(List continued on next page.)

*Primary Examiner*—John M. Ford
*Attorney, Agent, or Firm*—Finnegan, Henderson, Farabow, Garrett & Dunner, L.L.P.

[57] ABSTRACT

The invention relates to a process for the preparation of cephem prodrug esters of the formula:

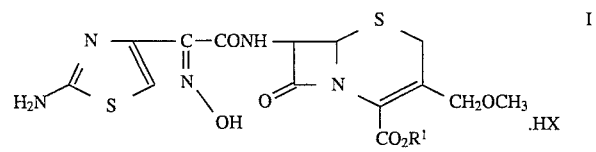

in which $R^1$ is $C_1$–$C_5$-alkanoyloxy-$C_1$–$C_3$-alkyl or $C_1$–$C_5$-alkoxycarbonyloxy-$C_1$–$C_3$-alkyl and X is an inorganic or organic anion, and in which the hydroxyimino group is present in the syn-form.

5 Claims, No Drawings

OTHER PUBLICATIONS

"Beta–Lactam Compounds", Chemical Abstracts, 102:220658k (1985).

"Cephalosporin derivatives", Chemical Abstracts, 102:220657j (1985).

"Antibiotic Activity of CL 118,673, a New Oral Cephalosporin", N. A. Kuck et al., Recent Advances In Chemotherapy, Proceedings of the 14th Int'l. Congress of Chemotherapy, Antimicrobial Section 2, pp. 1137–1138 (1985).

Improved Synthesis of an Ester–Type Prodrug, 1–Acetoxyethyl 7–[(Z)–2–(2–Aminothiazol–4–yl)–2– Hydroxyiminoacetamido]–3–[(Z)–1–Propenyl]–3–Cephem–4– Carboxylate (BMY–28271), Hajime Kamachi et al., The Journal of Antibiotics, vol. XLIII (12):1564–1572 (1990).

In Vivo Evaluation of Tigemonam, a Novel Oral Monobactam, Clark et al., Antimicrobial Agents and Chemotherapy, Feb. 1987, vol. 31, No. 2, pp. 226–229.

Pharmacokinetic and In Vivo Studies with Azithromycin (CP–62,993), a New Macrolike with an Extended Half–Life and Excellent Tissue Distribution, Antimicrobial Agents and Chemotherapy, Dec. 1987, vol. 31, No. 12, pp. 1948–1954.

Pharmacokinetics of FK482, A New Orally Active Cephalosporin, In Animals Sakamoto et al., The Journal of Antibiotics, vol. XLI(12):1896–1905 (1988).

Studies on Orally Active Cephalosporin Esters. II. Chemical Stability of Pivaloyloxymethyl Esters in Phosphate Buffer Solution, Miyauchi et al. Chemical and Pharmaceutical Bulletin, 37(9) 2369–2374 (1989).

Studies on Orally Active Cephalosporin Esters. IV. Effect of the C–3 Substituent of Cephalosporin on the Gastrointestinal Absorption in Mice, Chemical and Pharmaceutical Bulletin, 37(12) 3272–3276 (1989).

Synthesis and Mechanisms of Decomposition of Some Cephalosporin Prodrugs, J. of Pharm. Sciences, vol. 79, No. 9, (1990), Saab et al.

Uptake of Cephalosporin, Cephalexin, by a Dipeptide Transport carrier in the Human Intestinal Cell Line, Caco–2, Biochimica et Biophysica Acta, Dantzig et al., 1027 (1990) 211–217.

Drug Chirality—Impact on Pharmaceutical Regulations, Conference Documentation, Oct. 24th & 25th, 1990, The London Press Centre, London EC4.

The Relationship of Absorption Characteristics and Gastrointestinal Side Effects of Oral Antimicrobial Agents, Clinical Therapeutics, Grossman, vol. 13, No. 1, pp. 189–193 (1991).

Absolute Bioavailability of Cefprozil after Oral Administration in Beagles Antimicrobial Agents and Chemotherapy, Barbhaiya, et al. Mar. 1992, vol. 36, No. 3, pp. 687–689.

Comparative Pharmacokinetics of SCE–2787 and Related Antibiotics in Experimental Animals, Antimicrobial Agents and Chemotherapy, Kita et al. vol. 36, No. 11, pp. 2481–2486 (1992).

RU 29 246, The Active Compound of the Cephalosporin Prodrug–Ester HR 916 III. Pharmacokinetic Properties and Antibacterial Activity in vivo, The Journal of Antibiotics, vol. 45, No. 6, pp. 922–931 (1992).

Pharmacokinetics of Cefpirome Administered Intravenously or Intramuscularly to Rats and Dogs, Journal of Atimicrobial Chemotherapy, Isert, 29, Suppl. A., 31–37 (1992).

PROCESS FOR THE PREPARATION OF CEPHEM PRODRUG ESTERS

This application is a continuation, of application Ser. No. 08/016,562, filed Feb. 11, 1993, now abandoned.

The invention relates to a process for the preparation of cephem prodrug esters of the formula

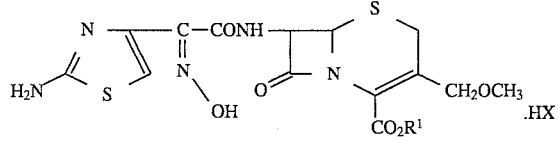

in which $R^1$ is $C_1$–$C_5$-alkanoyloxy-$C_1$–$C_3$-alkyl or $C_1$–$C_5$-alkoxycarbonyloxy-$C_1$–$C_3$-alkyl and X is an inorganic or organic anion, and in which the hydroxyimino group is present in the syn-form, which comprises allowing a compound of the formula II

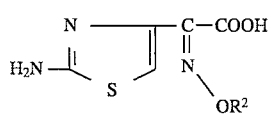

in which $R^2$ is a protective group which can be removed by acid hydrolysis, to react with a bis(benzothiazol-2-yl) disulfide of the formula VI

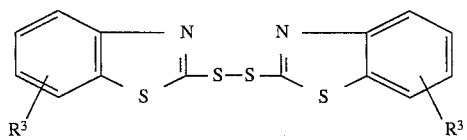

in which $R^3$ is hydrogen, $C_1$–$C_6$-alkyl, $C_2$–$C_6$-alkenyl, $C_3$–$C_6$-alkynyl, $C_1$–$C_6$-alkyloxy, $C_2$–$C_6$-alkenyloxy, $C_3$–$C_6$-alkynyloxy, hydroxyl, acetoxy, halogen, nitro, amino, carboxyl or the sulfo group, and triphenylphosphine in an inert solvent, in the presence of a tertiary amine, to give a compound of the formula V

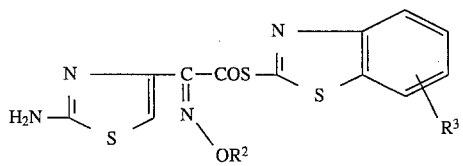

in which $R^2$ and $R^3$ have the abovementioned meanings, then reacting this compound with a 7-aminoceph-3-em-4-carboxylic acid ester of the formula III

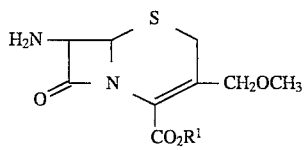

in which $R^1$ has the abovementioned meaning, in inert organic or dipolar aprotic solvents at temperatures between 0° and +80° C. and treating the resulting oxime-protected compound of the formula IV

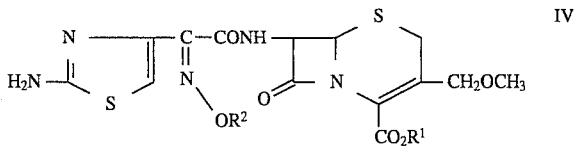

in which $R^1$ and $R^2$ have the abovementioned meanings and in which the protected oxime group is present in the syn-form, with inorganic acids or with aliphatic or aromatic sulfonic acids in organic solvents at temperatures between +20° and +110° C. to form the compound of the formula I.

Possible preferred radicals are the following:

$R^1$=acetoxymethyl, propionyloxymethyl, isopropionyloxymethyl, N-butyryloxymethyl, isobutyryloxymethyl, 2,2-dimethylpropionyloxymethyl, isovaleryloxymethyl, 1-acetoxy-1-ethyl, 1-acetoxy-1-propyl, 2,2-dimethylpropionyloxy-1-ethyl, 1-methoxycarbonyloxy-1-ethyl, 1-ethoxycarbonyloxy-1-ethyl, 1-isopropoxycarbonyloxyethyl or methoxycarbonyloxymethyl;

$R^2$=$C(C_6H_5)_3$, tetrahydropyranyl or 2-methoxy-2-propyl;

$R^3$=hydrogen, methyl, ethyl, propyl, methoxy, ethoxy, propoxy, isopropoxy or chlorine and $X=Cl^-$, $Br^-$, $HSO_4^-$, $CH_3SO_3^-$, $C_2H_5SO_3^-$, $C_6H_5SO_3^-$, p-$CH_3$—$C_6H_4$—$SO_3^-$ or p-$Cl$—$C_6H_4$—$SO_3^-$.

A particularly preferred radical for $R^1$ is 2,2-dimethylpropionyloxy-1-ethyl, in particular in the form of the pure (S)- or (R)-diastereomers, very particularly in the form of the pure (S)-diastereomer.

The reaction of the compound of the formula II with bis(benzothiazol-2-yl) disulfide of the formula VI and triphenylphosphine is carried out in an inert solvent, preferably in dichloromethane or ethyl acetate, in the presence of a tertiary amine, such as, for example, triethylamine or diisopropylamine. The compound of the formula V where $R^2$=$C(C_6H_5)_3$ and $R^3$=H is obtained in high yield and in very pure form using 1–2 mols of triethylamine. The same applies for the compound V where $R^2$=$C(C_6H_5)_3$ and $R^3$=6-ethoxy or 5-chloro.

The reaction of the compounds of the formula V with the aminocephem compound of the formula III is carried out in inert organic solvents such as ethyl acetate, dichloromethane, tetrahydrofuran or dipolar aprotic solvents such as dimethylformamide, dimethylacetamide or dimethyl sulfoxide at temperatures between 0° and +80°, preferably between 20° and 50° C. In the case of the compound of the formula V where $R^2$=$C(C_6H_5)_3$, dipolar aprotic solvents are preferably used because of its poor solubility. The reaction products of the formula IV are in this case isolated in a simple manner by pouring the reaction mixture into water, filtering off the precipitated product with suction and drying.

The starting compounds of the formula III can be either diastereomer mixtures or pure (S)- or (R)-diastereomers, where, for example, the compounds of the formula III where $R^1$=—CH(CH$_3$)OCOC(CH$_3$)$_3$ are known in the (S)- and (R)- form from German Patent Application No. P 41 16 937.9 which corresponds to co-pending U.S. application Ser. No. 07/886,143, filed May,21, 1992, being examined in Examining Group 1202, now abandoned.

The compounds of the formula IV are prepared according to the invention by removal of the oxime protective group by means of equivalent amounts or a slight excess of the abovementioned inorganic acids or organic sulfonic acids, a particular advantage of the process according to the invention lying in the fact that the removal of the protective group and the formation of the final substance in the desired physiologically tolerable salt form takes place in one step.

Suitable solvents are organic solvents such as alcohols, esters, ethers or ketones. Preferably, alcohols such as methanol, ethanol, n-propanol, isopropanol or the isomeric butanols are used. Those solvents from which the final product of the formula I precipitates from the reaction mixture as a salt (x HX) are particularly preferred. In the specific case according to the invention of the compounds of the formula I where $R^1$=(S)-2,2-dimethylpropionyloxy-1-ethyl and $R^2$=trityl or tetrahydropyranyl, this is preferably n-propanol as the solvent and p-toluenesulfonic acid as the agent removing the protective groups. The reaction temperatures are between +20° and +110° C., preferably between +50° and +100° C. A temperature between +70° and +100° C. is particularly preferred. After cooling the reaction mixture, filtering off with suction and drying, the final product is obtained in pure form as a tosylate salt.

The literature processes proved to be not very suitable. In cephalosporin chemistry, for example in EP-A 355,821, the trityl group is removed exclusively in strongly acidic solution, for example in 90% aqueous formic acid or in trifluoroacetic acid. Protective group removal and salt formation in each case proceed in separate reaction steps. The particular advantage of the one-step process according to the invention is illustrated by the following table for the preparation of the compounds according to the invention where $R^1$=(S)—CH(CH$_3$)OCOC(CH$_3$)$_3$ (Example 5 or 7) and $R^1$=CH(CH$_3$)OCOOCH(CH$_3$)$_2$ (Example 9). The final substances are formed both in higher yield and in purer form.

Comparative yields and purities in the preparation of the compounds of the formula I, $R^1$ = (S)—CH(CH$_3$)OCOC(CH$_3$)$_3$, as the tosylate and $R^1$ = (S,R)—CH(CH$_3$)—OCOOCH(CH$_3$)$_2$

| Example | Process | Yield % of theory | Purity[1] (HPLC) | Preparation Process for the precursor IV, R2 = trityl |
|---|---|---|---|---|
| 5 | This application | 86 | 100 | Thioester |
|  | EP-A 355,821 (HCOOH) | 73.5 | 95 |  |
| 7 | This application | 77 | 99 | Sulfonic anhydride |
|  | EP-A 355,821 | 69 | 96 |  |
| 9 | This application | 52 | 100 | Thioester |
|  | EP-A 355,821 (HCOOH) | 13 | 96 |  |

[1]Based on product, Example 5 = 100%

The invention furthermore relates to the compound of the formula II'

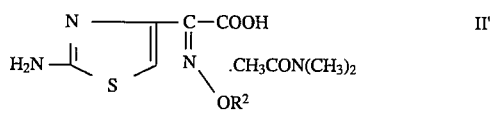

where $R^2$=trityl, which is present as a CH$_3$CON(CH$_3$)$_2$ adduct and to a novel process for the preparation of this compound of the formula II', which comprises reacting ethyl 2-aminothiazol-4-yl-2-hydroxyiminoacetate with triphenylmethyl chloride and potassium tert-butylate at room temperature in inert solvents, hydrolyzing the ethyl ester formed and treating the crude acid obtained with N,N-dimethylacetamide at temperatures between +20° and +70° C.

A similar process for the preparation of compounds of the formula II' where $R^2$=trityl is known from EP-A 355,821. The disadvantages of the process described therein comprise, inter alia, the use of hazardous sodium hydride, whose utilization on a large scale requires costly precautionary measures. Using the simpler-to-handle potassium tert-butylate as an HCl-removing agent, the tritylation proceeds smoothly at room temperature in inert solvents such as ethers or esters, preferably in tetrahydrofuran. After hydrolysis, the crude O-tritylcarboxylic acid is treated with N,N-dimethylacetamide at temperatures between +20° and +70° C., the adduct of the formula II' being formed in highly pure form and in high yield.

The novel compound of the formula II' where $R^2$=trityl can be reacted in high yield with the compounds of the formula III to give the compounds of the formula IV.

The invention furthermore relates to the compound of the formula II''

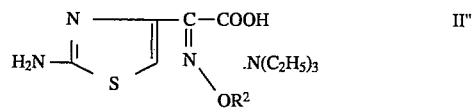 II'' where $R^2$=

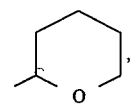

which is present as the triethylamine salt and which can also be reacted in high yield with the compounds of the formula III to give the compounds of the formula IV.

This reaction proceeds after activation by means of the acid chloride or the mixed anhydride, for example with sulfoacids, such as methane-, benzene- and p-toluenesulfonic acid, or a thioester, for example the 2-benzothiazolyl thioester or the 6-ethoxy- or 5-chloro-2-benzothiazolyl thioester. Activation as the sulfonic anhydride or as the 2-benzothiazolyl thioester of the general formula V is preferred, in which $R^2$ is trityl or tetrahydropyran-2-yl and $R^3$ is hydrogen, ethoxy or chlorine.

The following exemplary embodiments for the compounds which can be prepared by the process according to the invention serve for the further illustration of the invention, but without restricting it thereto.

Abbreviations:

THP tetrahydropyran
DMAA N,N-dimethylacetamide

EXAMPLE 1

(Z)-2-(2-Aminothiazol-4-yl)-2-trityloxyiminoacetic acid. Adduct with N,N-dimethylacetamide 148 g (1.32 mol) of potassium tert-butylate are added in one portion at +2° C. with stirring and cooling to a suspension of 258.3 g (1.2 mol) of ethyl (Z)-2-(2-aminothiazol-4-yl)-2-hydroxyiminoacetate in 2 l of dry tetrahydrofuran. On warming to +4° C., the suspension changes color to red-brown. The mixture reaches room temperature without cooling after 30 minutes. It is stirred for a further hour and then cooled to 15° C., and 362.4 g (1.3 mol) of trityl chloride are added. Without external cooling, it is stirred for a further 5 hours, a maximum internal temperature of +39° C. being reached after about 2 hours. The suspension is then poured into a mixture of 1.5 l of ice-water and 1.2 l of diisopropyl ether, stirred for half an hour and left overnight at 5° C., and the precipitate is filtered off with suction and washed in portions with 1 l of water and 700 ml of diisopropyl ether. For hydrolysis, the still moist product is boiled for 3 hours with a solution of 67.4 g (1.2 mol) of potassium hydroxide in 1 l of water and 1.2 l of ethanol. After 2 hours, a clear, dark solution is present. It is cooled to 60° C., 1.2 l of ethyl acetate are added and the mixture is cooled to +10° C. and about 190 ml of 6N hydrochloric acid are added up to a pH of 4.0 with stirring in the course of 15 minutes. A crystalline precipitate is formed. After 16 hours at 5° C., it is filtered off with suction, washed with 1.5 l of water and then 1.5 l of diisopropyl ether in portions, and dried in vacuo at 80° C.

The crude acid is introduced into a mixture of 600 ml of dimethylacetamide and 1.2 l of toluene, stirred at 65° C. for 10 minutes, cooled in an ice-bath for 1 hour, filtered off with suction, washed with 800 ml of toluene in portions and dried in vacuo at 80° C.

Yield: 372 g of pale grey crystals (60% of theory), Dec. 179°–181° C.

$^1$H-NMR (DMSO-$d_6$, 270 MHz): δ=1.96 (s, 3H, CH$_3$CO); 2.80 (s, 3H, NCH$_3$); 2.95 (s, 3H, NCH$_3$); 6.69 (s, 1H, thiazole); 7.2–7.42 (m, 15H, trityl)

EXAMPLE 2

(Z)-2-(2-Aminothiazol-4-yl)-2-(tetrahydropyran-2-yl)-oxyiminoacetic Acid Triethylamine Salt 10.5 g (90 mmol) of O-(tetrahydropyran-2-yl)hydroxylamine are added in portions to 14.6 g (85 mmol) of 2-aminothiazole-4-yl-glyoxylic acid and 7.4 ml (53 mmol) of triethylamine in 250 ml of methanol. The suspension is stirred at room temperature for 1.5 hours. A further 5.2 ml (38 mmol) of triethylamine are added, whereupon a pale yellow solution is formed. The mixture is left overnight at room temperature, the solvent is removed in vacuo and the initially oily residue is digested with ether whereupon crystallization occurs. The solid is filtered off with suction, washed with ether and dried.

Yield: 30.2 g (96% of theory), dec. 141°–144° C.

$^1$H-NMR (DMSO-$d_6$, 270 MHz): δ=1.16 (t, 9H, NRt$_3$); 1.3–1.8 (m, 6 THP-H); 2.98 (q, 6H, NEt$_3$); 3.4 and 3.88 (each 1m, 2 THP-H); 5.10 (s, 1 THP-H); 6.62 (s, 1H, thiazole ); 7.0 (s, 2H, NH$_2$)

EXAMPLE 3

2-Benzothiazolyl (Z)-2-(2-aminothiazol-4-yl)-2-trityloxyiminothioacetate

A suspension of 125.9 g (480 mmol) of triphenylphosphine and 159.5 g (480 mmol) of bis(benzothiazol-2-yl) disulfide in 800 ml of dry dichloromethane is stirred at room temperature for 60 minutes. It is cooled to 15° C. and 206.6 g (400 mmol) of (Z)-2-(2-aminothiazol-4-yl)-2-trityloxyiminoacetic acid-DMMA adduct are introduced in one portion. On warming to 26° C., a readily stirrable suspension is formed. It is stirred at room temperature for 50 minutes and cooled to 10° C., and 40.5 g (400 mmol) of triethylamine are added dropwise in the course of 25 minutes. The suspension is stirred at room temperature for a further 5 hours and then cooled to 5° C., and the solid is filtered off with suction, washed twice with 30 ml of dichloromethane each time (10° C.) and three times with 50 ml of diisopropyl ether each time and dried in vacuo at 50° C.

Yield: 222.6 g (96% of theory), dec. 187°–189° C.

Content according to HPLC: 99.3%, By-product 0.3% of 2-mercaptobenzothiazole $^1$H-NMR (DMSO-$d_6$, 270 MHz): δ=6.84 (s, thiazole-H); 7.22–7.42 (m, 15H, trityl); 7.62 (2 arom. H); 8.12 and 8.28 (each 1 arom. H)

EXAMPLE 4

2-Benzothiazolyl (Z)-2-(2-Aminothiazol-4-yl)-2-(tetrahydropyran-2-yl)-oxyiminothioacetate 59.0 g (225 mmol) of triphenylphosphine, 74.8 g (225 mmol) of bis(benzothiazol-2-yl) disulfide and 64.1 g (172 mmol) of (Z)-2-(2-aminothiazol-4-yl)-2-(tetrahydropyran-2-yl)oxyiminoacetic acid triethylamine salt in 630 ml of dichloromethane are reacted as described in Example 3. After stirring at room temperature for 6 hours, the mixture is cooled to 5° C., and the precipitate is filtered off with suction and washed with a little cold dichloromethane.

Yield: 53.7 g (72% of theory), dec. 158°–161° C.

$^1$H-NMR (CDCl$_3$, 270 MHz): δ=1.4–2.0 (m, 6 THP-H); 3.6–4.0 (m, 2 THP-H); 5.50 (s, 1 THP-H); 6.62 (s, 2H, NH$_2$); 6.85 (s, thiazole-H); 7.50 (2 arom. H); 7.94 and 8.10 (each 1 arom. H)

EXAMPLE 5

1-(1S)-(2,2-Dimethylpropionyloxy)ethyl 7-[2-(2-aminothiazol-4-yl)-2-(Z)-hydroxyiminoacetamido]-3-methoxymethyl-3-cephem-4-carboxylate p-toluenesulfonate 57.8 g (100 mmol) of 2-benzothiazolyl (Z)-2-(2-aminothiazol-4-yl)-2-trityloxyiminothioacetate and 33.5 g (90 mmol) of 1-(1S)-(2,2-dimethylpropionyloxy)ethyl 7-amino-3-methoxymethyl-3-cephem-4-carboxylate (S:R=97:3) are stirred at room temperature for 45 minutes in 450 ml of N,N-dimethylformamide (24°–28° C., weakly exothermic). The solution is allowed to run into 2.6 l of half-concentrated NaCl, the mixture is stirred for 10 minutes, and the resulting precipitate is filtered off with suction, washed three times with 100 ml of water each time and dried in vacuo.

Trityl Cleavage and Tosylate Formation

The mixture obtained from the trityl-protected title compound and 2-mercaptobenzothiazole is heated at 85°–90° C. for 30 minutes together with 21.3 g (112 mmol) of p-toluenesulfonic acid monohydrate in 450 ml of n-propanol. After 5 minutes, the deposition of a crystalline precipitate commences. The suspension is cooled to 15° C., and the solid is filtered off with suction, washed three times with 25 ml of n-propanol each time and with diisopropyl ether and dried in vacuo at 50° C. for 1 hour.

Yield: 55.4 g (86% of theory, colorless crystals, HPLC 100% content $^1$H-NMR (DMSO-$d_6$, 270 MHz): δ=1.15 (s, 9H, C(CH$_3$)$_3$; 1.48 (d, 3H, CH<u>CH$_3$</u>); 2.29 (s, 3H, tosyl-CH$_3$); 3.20 (s, 3H, OCH$_3$); 3.59 (AB, 2H, SCH$_2$); 4.14 (s, 2H, CH$_2$O); 5.24 (d, 1H, H-6); 5.85 (dd, 1H, H-7); 6.82 (s, 1H, thiazole-H); 6.87 (q, 1H <u>CH</u>CH$_3$); 7.11 and 7.48 (each 2h, AA'XX', tosyl-H); 8.0–9.0 (br, 3H, NH$_3$), 9.67 (d, 1H, amide-NH); 12.04 (s, 1H, NOH)

Trityl Cleavage With Formic Acid for Comparison

The mixture of the trityl-protected title compound and 2-mercaptobenzothiazole obtained from a similar 1/10 batch is stirred at room temperature for 1 hour in 60 ml of 80% formic acid. The triphenylcarbinol formed is filtered off and washed with 10 ml of 80% HCOOH, the filtrate is stirred into 500 ml of ice-water and the mixture is adjusted to pH 4.0 at 5°–10° C. by addition of 60 ml of conc. aqueous NH$_3$.

The precipitate is filtered off with suction, washed with water and dried.

Tosylate Formation

The amorphous product is dissolved in 20 ml of n-propanol together with 1.71 g (9 mmol) of p-toluenesulfonic acid hydrate. The precipitate formed is filtered off with suction after standing for 2 hours at 15° C., and washed three times with 4 ml of n-propanol each time and with diisopropyl ether. After drying, 5.25 g (73.5%) of the title compound are obtained. The NMR spectrum is identical to that of the compound obtained above. The purity by HPLC is 95% in comparison with the above compound.

EXAMPLE 6

Compound of Example 5 From the THP-Protected Thioester 5.2 g (11.9 mmol) of active ester from Example 4 and 4.03 g (10.8 mmol) of 1-(1S)-(2,2-dimethylpropionyloxy)ethyl 7-amino-3-methoxymethyl-3-cephem-4-carboxylate (S:R= 98:2) are reacted in 54 ml of DMF as in Example 5. The dried crude product is converted into the tosylate using 4.1 g (21.6 mmol) of p-toluenesulfonic acid monohydrate in 84 ml of n-propanol at 80°–85° C.

Yield: 6.4 g (83% of theory), colorless crystals

The compound is identical in all properties with that from Example 5.

EXAMPLE 7

Compound of Example 5

Sulfonic Anhydride Process Using the Trityl Acid From Example 1

5.37 g (53 mmol) of triethylamine are added at 15° C. under argon to a suspension of 27.4 g (53 mmol) of (Z)-2-(aminothiazol-4-yl)-2-trityloxyiminoacetic acid-DMAA adduct (Example 1) in 90 ml of N,N-dimethylacetamide and 10 ml of dry acetone. The suspension is then cooled to –20° C. and 9.91 g (52 mmol) of p-toluenesulfonyl chloride are added. The mixture is stirred at –14° to –10° C. for 2¼ hours. The almost clear yellowish solution formed is then cooled to –35° C. and a solution of 14.9 g (40 mmol) of 1-(1S)-(2,2-dimethylpropionyloxy)ethyl 7-amino-3-methoxymethyl-3-cephem-4-carboxylate (S:R=97:3) in 30 ml of DMAA is added dropwise during the course of 15 minutes. The mixture is stirred at –25° C. for 45 minutes. The reaction solution is introduced into a mixture of 300 g of ice and 300 ml of saturated $NaHCO_3$ solution, the suspension is stirred for 2 hours, and the solid is filtered off with suction and washed three times with 200 ml of water each time. The moist precipitate is dissolved in 600 ml of ethyl acetate, washed three times with 200 ml of half-concentrated $NaHCO_3$ solution, three times with 100 ml of water and twice with 100 ml of saturated NaCl solution each time, dried with $MgSO_4$ and evaporated.

Trityl Cleavage and Tosylate Formation

After addition of 7.62 g (40 mmol) of p-toluenesulfonic acid hydrate and 200 ml of n-propanol, the amorphous residue is heated at 85°–90° for 30 minutes. A crystalline precipitate is formed which, after cooling to 15° C., is filtered off with suction and washed three times with 10 ml of n-propanol each time and with diisopropyl ether. After drying in vacuo at 50° C., 22.0 g (77% of theory) of colorless crystals are obtained. HPLC: 99% in comparison with the product from Example 5. The NMR spectrum is identical with that of the product from Example 5.

Trityl Cleavage With Formic Acid for Comparison

The above batch is carried out analogously in half the size using 7.45 g (20 mmol) of 1-(1S)-(2,2-dimethylpropionyloxy)ethyl 7-amino-3-methoxymethyl-3-cephem-4-carboxylate. The amorphous trityl-protected title compound is dissolved in 120 ml of 80% aqueous formic acid and stirred at room temperature for 1 hour. The precipitated triphenylcarbinol is filtered off with suction and washed with 20 ml of 80% HCOOH. The filtrate is stirred into 700 ml of ice-water and brought to pH 4.0 by addition of 120 ml of conc. $NH_3$ at 10° C. The precipitate is filtered off with suction, washed with water and dried over $P_2O_5$ at 1 mm Hg.

Tosylate Formation

The amorphous product obtained (9.3 g) is dissolved in 37 ml of n-propanol and treated with a solution of 3.0 g (16 mmol) of p-toluenesulfonic acid monohydrate in 8 ml of n-propanol. The mixture is left overnight in a refrigerator, and the solid is filtered off with suction, washed twice with 5 ml of n-propanol each time, then with diisopropyl ether and dried in vacuo over $P_2O_5$.

Yield: 9.85 g (69% of theory)

Purity according to HPLC 96% in comparison with the product from Example 5.

The NMR spectrum is identical with that of the product from Example 5.

EXAMPLE 8

Compound of Example 5

Sulfonic Anhydride Process Using the THP Acid From Example 2

A solution of 5.35 g (14.36 mmol) of (Z)-2-(2-aminothiazol-4-yl)-2-tetrahydropyran-2-yl)oxyiminoacetic acid triethylamine salt in 18 ml of N,N-dimethylacetamide and 2 ml of dry acetone is cooled to –20° C. and a solution of 2.61 g (13.7 mmol) of p-toluenesulfonyl chloride in 5 ml of DMAA is added. The mixture is stirred at –15° to –10° C. for 1½ hours and then cooled to –30° C., and a solution of 3.73 g (10 mmol) of 1-(1S)-(2,2-dimethylpropionyloxy)ethyl 7-amino-3-methoxymethyl-3-cephem-4-carboxylate in 9 ml of DMAA is added dropwise in the course of 10 minutes. The solution is stirred at –25° C. for a further 45 minutes. It is then stirred into a mixture of 100 g of ice and 100 ml of saturated $NaHCO_3$ solution, the mixture is stirred for one hour, the deposited precipitate is filtered off with suction, washed with water and dissolved in 200 ml of ethyl acetate, and the solution is washed with 50 ml of saturated $NaHCO_3$ solution, with water and twice with 50 ml of saturated NaCl solution each time. After drying with $MgSO_4$ it is evaporated.

THP Cleavage and Tosylate Formation

The amorphous residue (7.3 g) is dissolved in 50 ml of n-propanol with 2.85 g (15 mmol) of p-toluenesulfonic acid hydrate and heated at 90° C. for 25 minutes. After 2 minutes, the separation of a crystalline precipitate commences. The suspension is cooled to 15° C., and the solid is filtered off with suction, washed three times with 8 ml of n-propanol each time and with diisopropyl ether and dried in vacuo at 50° C. for 1 hour.

Yield: 5.3 g (74% of theory) of colorless crystals

Purity according to HPLC: 99% in comparison with the product from Example 5.

The NMR spectrum is identical with that of the compound from Example 5.

EXAMPLE 9

1-(1R,S)-(isopropoxycarbonyloxy)ethyl 7-[2-(2-aminothiazol-4-yl)-2-(Z)-hydroxyiminoacetamido]-3-methoxymethyl-3-cephem-4-carboxylate p-toluenesulfonate 905 mg (2.42 mmol) of 1-(1R,S)-(isopropyloxycarbonyloxy)ethyl 7-amino-3-methoxymethyl-3-cephem-4-carboxylate and 1.5 g (2.6 mmol) of 2-benzothiazolyl (Z)-2-(2-aminothiazol-4-yl)-2-trityloxyiminothioacetate are reacted in 10 ml of N,N-dimethylformamide analogously to Example 5. The trityl-protected title compound is heated at 90° C. for 25 minutes with 475 mg (2.5 mmol) of p-toluenesulfonic acid hydrate in 10 ml of n-propanol. After cooling, 900 mg (52% of theory) of the title compound crystallize. If the trityl group is first removed with formic acid and the tosylate is then formed analogously to Example 5, the yield is 231 mg (13% of theory).

$^1$H-NMR(DMSO-$d_6$, 270 MHz): δ=1.24 (2d, 6H, CH(C$\underline{H}_3$)$_2$); 1.50 (d, 3H, CHC$\underline{H}_3$); 2.29 (s, 3H, tosyl-CH$_3$); 3.21 (s, 3H, OCH$_3$); 3.60 (AB, 2H, SCH$_2$); 4.17 (s, 2H, CH$_2$O); 4.80 (m, 1H, C$\underline{H}$(CH$_3$)$_2$); 5.84 (dd, 1H, H-7); 6.80 (q, 1H, C$\underline{H}$CH$_3$; 6.83 (s, 1H, thiazole-H); 7.12 and 7.48 (each 2H, AA'XX', tosyl-H); 9.68 (d, 1H, amide-NH); 12.12 (s, 1H, NOH).

EXAMPLE 10

6-Ethoxy-2-benzothiazolyl (Z)-2-(2-aminothiazol-4-yl)-2-trityloxyiminothioacetate A suspension of 10.5 g (40 mmol) of triphenylphosphine and 16.8 g (40 mmol) of bis(6-ethoxy-benzothiazol-2-yl) disulfide in 70 ml of dry dichloromethane is stirred at room temperature for 35 minutes. 17.2 g (33.3 mmol ) of (Z)-2-(2-aminothiazol-4-yl)-2-trityloxyiminoacetic acid/DMAA adduct are added at 12° C. The suspension is stirred for 45 minutes and cooled to 12° C., 3.36 g (33.3 mmol) of triethylamine are added and the mixture is stirred at room temperature for 4 hours. The solid is filtered off with suction, washed with 150 ml of dichloromethane and 150 ml of diisopropyl ether in portions and dried in vacuo.

Yield: 20.6 g (quantitative), dec. 218° C.

$^1$H-NMR(DMSO-$d_6$; 200 MHz): δ=1.41 (t, 3H, CH$_2$—C$\underline{H}_3$); 4.16 (q, 2H, C$\underline{H}_2$CH$_3$); 6.82 (s, thiazole-H); 7.18–7.42 (m, 16 arom. H); 7.80 and 8.00 (each 1 arom. H).

EXAMPLE 11

5-Chloro-2-benzothiazolyl (Z)-2-(2-aminothiazol-4-yl)-2-trityloxyiminothioacetate 2.6 g (10 mmol) of triphenylphosphine, 4.0 g (10 mmol) of bis(5-chlorobenzothiazol-2-yl) disulfide, 4.3 g (8.35 mmol) of (Z)-2-(2-aminothiazol-4-yl)-2-trityloxyiminoacetic acid/DMAA adduct and 0.84 g (8.35 mmol) of triethylamine are reacted in 20 ml of dichloromethane as described in Example 10. The suspension is stirred at room temperature for 20 hours, and the precipitate is filtered off with suction, washed with 40 ml of dichloromethane and 40 ml of diisopropyl ether and dried in vacuo.

Yield: 5.0 g (quantitative), dec. 192° C.

$^1$H-NMR (DMSO-$d_6$; 200 MHz): δ=6.86 (s, thiazole-H); 7.20–7.44 (m, 15 arom. H); 7.65, 8.20 and 8.32 (each 1 arom. H).

EXAMPLE 12

Compound of Example 5 From the Active Ester of Example 10

3.12 g (5 mmol) of 6-ethoxy-2-benzothiazolyl (Z)-2-(2-aminothiazol-4-yl)-2-trityloxyiminothioacetate and 1.9 g (5.1 mmol) of 1-(1S)-(2,2-dimethylpropionyloxy)ethyl 7-amino-3-methoxymethyl-3-cephem-4-carboxylate are stirred at room temperature for 18 hours in 40 ml of N-N-dimethylformamide. The clear yellow solution obtained is allowed to run into 300 ml of half-concentrated sodium chloride solution, and the precipitate is filtered off with suction, washed four times with 20 ml of water each time and dried in vacuo.

Yield: 4.76 g (95.6% of theory)

The mixture obtained from the trityl-protected title compound and 6-ethoxy-2-mercaptobenzothiazole is heated at 90° C. for 30 minutes in 25 ml of n-propanol together with 1.05 g (5.5 mmol) of p-toluenesulfonic acid monohydrate. After 10 minutes, the deposition of a precipitate begins. After the temperature has reached 30° C., the precipitate is filtered off with suction and washed three times with 5 ml of n-propanol and with diisopropyl ether each time. After drying in vacuo, 2.60 g of colorless crystals are obtained (72.8% of theory). The compound is identical in all properties to that from Example 5.

EXAMPLE 13

Compound of Example 5 From the Active Ester of Example 11

3.07 g (5 mmol) of 5-chloro-2-benzothiazolyl (Z)-2-(2-aminothiazol-4-yl)-2-trityloxyiminothioacetate and 1.9 g (5.1 mmol) of 1-(1S)-(2,2-dimethylpropionyloxy)ethyl 7-amino-3-methoxymethyl-3-cephem-4-carboxylate are stirred at room temperature for 2 hours in 40 ml of N,N-dimethylformamide solution. The solution is worked up as described in Example 12, and the mixture of trityl-protected title compound and 5-chloro-2-mercaptobenzothiazole is stirred at 90° C. for 30 minutes in 25 ml of n-propanol in 1.05 g (5.5 mmol) of p-toluenesulfonic acid monohydrate. The precipitate formed is filtered off with suction after cooling to 15° C., washed with n-propanol and diisopropyl ether and dried in vacuo.

Yield: 2.73 g (76.5% of theory) of colorless crystals. The compound is identical in all properties to that from Example 5.

We claim:

1. A process for the preparation of a compound of the formula I

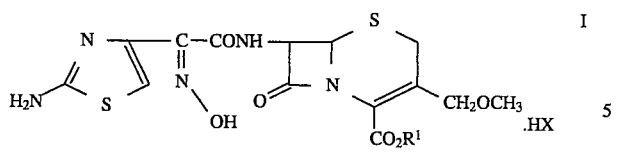

in which $R^1$ is $C_1$–$C_5$-alkanoyloxy-$C_1$–$C_3$-alkyl or $C_1$–$C_5$-alkoxycarbonyloxy-$C_1$–$C_3$-alkyl and X is an inorganic or organic anion, and in which the hydroxyimino group is present in the syn-form, which comprises allowing a compound of the formula II

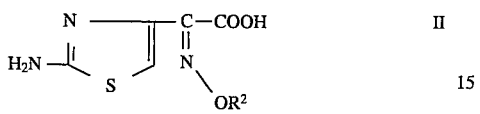

in which $R^2$ is a protective group which can be removed by acid hydrolysis, to react with a bis(benzothiazol-2-yl) disulfide of the formula VI

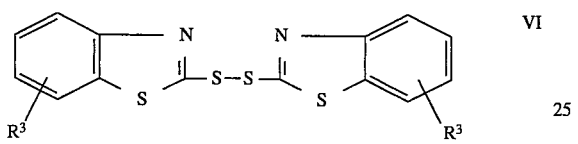

in which $R^3$ is hydrogen, $C_1$–$C_6$-alkyl, $C_2$–$C_6$-alkenyl, $C_3$–$C_6$-alkynyl, $C_1$–$C_6$-alkyloxy, $C_2$–$C_6$-alkenyloxy, $C_3$–$C_6$-alkynyloxy, hydroxyl, acetoxy, halogen, nitro, amino, carboxyl or the sulfo group, and triphenylphosphine in an inert solvent, in the presence of a tertiary amine, to give a compound of the formula V

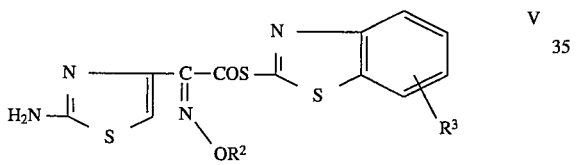

in which $R^2$ and $R^3$ have the abovementioned meanings, then reacting the compound of formula V with a 7-aminoceph-3-em-4-carboxylic acid ester of the formula III

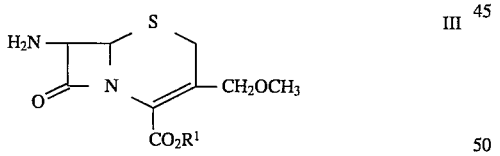

in which $R^1$ has the abovementioned meaning, in inert organic or dipolar aprotic solvents at temperatures between 0° and +80° C. and treating the resulting oxime-protected compound of the formula IV

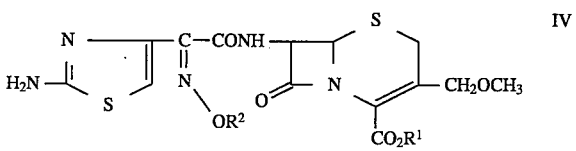

in which $R^1$ and $R^2$ have the abovementioned meanings and in which the protected oxime group is present in the syn-form, with inorganic acids or with aliphatic or aromatic sulfonic acids in organic solvents at temperatures between +20° and +110° C. whereby the protective group $R^2$ is removed and a salt is formed in one step to form the compound of the formula I.

2. The process for the preparation of a compound of the formula I as claimed in claim 1, wherein $R^1$ is acetoxymethyl, propionyloxymethyl, isopropionyloxymethyl, N-butyryloxymethyl, isobutyryloxymethyl, 2,2-dimethylpropionyloxymethyl, isovaleryloxymethyl, 1-acetoxy-1-ethyl, 1-acetoxy-1-propyl, 2,2-dimethylpropionyloxy-1-ethyl, 1-methoxycarbonyloxy-1-ethyl, 1-ethoxycarbonyloxy-1-ethyl, 1-isopropoxycarbonyloxyethyl or methoxycarbonyloxymethyl;

$R^2$ is $C(C_6H_5)_3$, tetrahydropyranyl or 2-methoxy-2-propyl;

$R^3$ is hydrogen, methyl, ethyl, propyl, methoxy, ethoxy, propoxy, isopropoxy or chlorine and X is $Cl^-$, $Br^-$, $HSO_4^-$, $CH_3SO_3^-$, $C_2H_5SO_3^-$, $C_6H_5SO_3^-$, p-$CH_3$—$C_6H_4$—$SO_3^-$ or p-Cl—$C_6H_4$—$SO_3^-$.

3. The process for the preparation of a compound of the formula I as claimed in claims 1 or 2, wherein, in the reaction of the compound of the formula IV with inorganic acids or with aliphatic or aromatic sulfonic acids, HCl, HBr or $H_2SO_4$ or methane-, ethane-, benzene-, p-toluene- or 2,4-dichlorobenzenesulfonic acid is employed.

4. The process for the preparation of a compound of the formula I as claimed in claim 1, wherein $R^1$ is 2,2-dimethylpropionyloxy-1-ethyl in the (R)- or (S)- form.

5. The process for the preparation of a compound of the formula I as claimed in claim 4, wherein $R^1$ is 2,2-dimethylpropionyloxy-1-ethyl in the (S)- form.

\* \* \* \* \*